United States Patent [19]

Reddy

[11] Patent Number: 4,622,304
[45] Date of Patent: Nov. 11, 1986

[54] METHOD OF GROWING CHEESE STARTER MICROORGANISMS

[75] Inventor: Malireddy S. Reddy, Aurora, Colo.

[73] Assignee: Mid-America Dairymen, Inc., Springfield, Mo.

[21] Appl. No.: 756,927

[22] Filed: Jul. 19, 1985

Related U.S. Application Data

[63] Continuation of Ser. No. 483,507, Apr. 11, 1983, abandoned.

[51] Int. Cl.$^4$ .................. C12N 1/20; A23C 19/02; A23C 21/02
[52] U.S. Cl. ...................................... 435/253; 426/36; 426/41; 426/43
[58] Field of Search ................. 426/34, 36, 41, 42, 426/43; 435/253

[56] References Cited

U.S. PATENT DOCUMENTS

| | | | |
|---|---|---|---|
| Re. 28,276 | 12/1974 | Farr | 426/43 X |
| 3,998,700 | 12/1976 | Reinbold et al. | 426/43 X |
| 4,282,255 | 8/1981 | Sandine et al. | 426/34 X |
| 4,289,788 | 9/1981 | Cajigas | 426/41 X |
| 4,372,979 | 2/1983 | Reinbold et al. | 426/36 |

OTHER PUBLICATIONS

Limsointin, et al., New Zealand Journal of Dairy Science and Technology, vol. 15, 1980, (pp. 219-224).
Richardson, et al., Lactic Culture System, Utah Agricultural Experiment Station, Research Report 42, Aug. 1979, pp. 1-7.

*Primary Examiner*—David M. Naff
*Attorney, Agent, or Firm*—Schmidt, Johnson, Hovey & Williams

[57] ABSTRACT

An improved method of growing acid-producing microorganisms (bacteria) used in cheese making is provided which gives enhanced bacterial counts and activities, and yields proper coccus/rod ratios in the case of mixed cultures used for making Italian cheeses such as mozzarella. The preferred method involves inoculating a starter medium with the appropriate microorganisms, followed by initial incubation until the pH of the medium drops to about 3.9-5.5; at this point the pH is raised to about 5.5-7.5, typically by the addition of a base such as sodium hydroxide. The medium is then allowed to further incubate to completion. In particularly preferred forms, the starter medium includes sweet whey, nonfat dry milk, and a minor proportion of lecithin, inasmuch as this medium gives enhanced results when used in conjunction with the improved method.

6 Claims, No Drawings

METHOD OF GROWING CHEESE STARTER MICROORGANISMS

This application is a continuation of application Ser. No. 483,507, filed Apr. 11, 1983 now abandoned.

BACKGROUND OF THE INVENTION

1. Field of the Invention

The present invention is broadly concerned with an improved method of growing or culturing acid-producing microorganisms used in cheese making. More particularly, it is concerned with an improved method which involves initially permitting an inoculated medium to incubate until the pH of the medium drops to an appropriate level, followed by raising of the pH and further incubation to completion. The method has been shown to give enhanced results, particularly in conjunction with a new lecithin-containing starter medium.

2. Description of the Prior Art

In the manufacture of natural cheese, milk in a cheese vat is inoculated with a minor amount (e.g., 2-4 percent) of a bulk starter providing the necessary culture of acid-forming microorganisms used for the particular cheese being manufactured. For example, in the case of Italian cheeses such as mozzarella, it is the usual practice to employ *Streptococcus thermophilus* together with one or more lactobacilli such as *Lactobacillus bulgaris*. In the art, the streptococci are generally referred by the short name of "coccus", while the lactobacilli are referred to as "rod" bacteria because of their appearance under microscopic examination.

The quantity and acitivity of cheese-making microorganisms can be critical to the overall outcome of the process and final cheese quality. Again referring to the Italian cheese, it has been found that, in order to make acceptable cheese, the ratio of coccus to rod organisms in the starters should be from about 1:1 to 5:1, the most preferable level being about 4:1. If these ratio considerations are not met, the final cheese product may be deficient in flavor or physical properties such as elasticity and "stringiness."

It is the universal practice among cheese makers to grow their bulk starters using relatively minor amounts of seed culture. In such techniques, the seed culture is inoculated into a starter medium, and allowed to incubate therein so that the culture cells will multiply to produce the desired bulk starter for use in cheese making. Here again, the types of starter media and the techniques used during the incubation process can have a relatively critical outcome on the quality of the final bulk starter, and hence on the cheese ultimately produced. A dilute dispersion of nonfat milk (e.g., 12 percent solids level) in water has long been considered the starter medium of choice. However, use of nonfat milk in this context is a relatively expensive proposition, and therefore cheese makers have in the past sought to use media of a less expensive nature which either eliminate nonfat milk entirely, or sharply limit its use by provision of substitute materials. Many of these proposed media include constituents such as whey or the like. Exemplary patents disclosing prior starter media include U.S. Pat. Nos. 3,998,700, 2,805,950, and 3,852,158.

The longstanding technique of starter incubation used by cheese makers has been to simply inoculate the medium (which is typically at or around neutral pH), while maintaining the medium in a heated condition (e.g., 102 degrees F.). During the incubation process the seed culture multiplies and produces acid; this in turn serves to drop the pH level of the medium down to a level of 4.0–5.0, at which time the titratable acidity of the medium is typically at an appropriate level and the incubation is then terminated by cooling to 40–50 degrees Fahrenheit. While this is the customary approach, workers in the art have devised a number of different operational methods which can, in certain circumstances, produce more or better quality cheese-making microorganisms. For example, researchers at the Utah State University have developed a lactic culture system which involves continuous neutralization of the starter medium during incubation. Specifically, use of this system involves a pH control system including pH probes, and means for injecting a base such as ammonia into the starter medium. Generally speaking, the starting pH of the medium is around 6.3, and, as the pH drops during incubation to a level of about 6.0, base is injected in order to bring the pH of the system back up to the desired 6.3 level. Accordingly, the pH of the medium using this technique is constantly maintained between 6.0 and 6.3, and is never allowed to decrease to the levels of acidity reached in traditional processes. While this approach (sometimes referred to in the art as "external pH control") has achieved substantial usage in the cheese making art, a number of problems remain. First, while the 6.0–6.3 pH range is sometimes preferable from the standpoint of bacterial growth, continual pH maintenance within this range can upset typical enzymatic systems and, in the case of Italian cheeses, the coccus/rod ratio ultimately obtained may be adversely affected. Moreover, in the traditional approach, the drop in pH to the 4.0–5.0 level has the effect to retarding the growth of pathogens; however, the external pH control system never permits the pH level to drop to this level, and accordingly pathogens which would otherwise be inactivated remain viable in the medium.

Another method developed in recent years is described in U.S. Pat. No. 4,282,255. This patent relates to a method for growing acid-producing bacteria wherein use is made of temporarily water insoluble neutralizing agents which are placed directly in the starter tank. These tablets or bodies include basic materials, and are designed to slowly and continuously release base in order to continuously maintain the pH level, typically between 5 and 7. In practice, and as disclosed in the referenced patent, these slow-release bodies require continual stirring or agitation of the starter tank. Such agitation has been found to present problems, inasmuch as it can interfere with proper cell growth and multiplication. Also, the slow-release pH control system disclosed in U.S. Pat. No. 4,282,255 (sometimes referred to in the art as "internal pH control"), suffers from the fact that the pH level is never allowed to decrease to a point where pathogens are completely killed.

In short, both the external and internal pH control systems involve an attempt to control pH within a relatively narrow band. Accordingly, a graph of pH versus time for these processes shows an initial pH drop to the desired range of pH control, followed by a generally horizontal graphical pattern. In the case of the external pH control, the graph typically is in the form of a "sawtooth" by virtue of periodic addition of base; on the other hand, the internal pH control typically generates a straighter graphical line in this region, by virtue of the slow, continual release of base in the starter media and consequent continual neutralization of acid as produced by the microorganisms.

SUMMARY OF THE INVENTION

The present invention provides a greatly improved method of growing acid-producing microorganisms used in cheese making processes. Broadly speaking, the process includes the steps of providing a starter medium in the form of a liquid, which may be any one of a number of conventional media, including reconstituted nonfat dry milk solids. The liquid medium is then inoculated with at least one cheese-making microorganism, and the medium is allowed to initially incubate until the pH of the latter drops to about 3.9–5.5, more preferably from about 4.5–5.3, and most preferably below about 5.0. The pH of the medium is thereafter raised, and the system is allowed to further incubate until completion.

In one particularly preferred form of the invention, the initial incubation step is carried out without addition of base and consequent neutralization of acid produced until the pH is lowered to the desired point, whereupon the pH is quickly raised at least about one pH unit and to a level of from about 5.5–7.5, and more preferably from about 6.3–6.5. Such relatively quick pH raising is most advantageously accomplished by direct addition of liquid base, such as a base selected from the group consisting of sodium hydroxide, potassium hydroxide, ammonium hydroxide, and calcium hydroxide, or any other suitable food grade base. Moreover, such quick pH elevation should be accomplished within a period of up to about 3 minutes.

Typically, the initial pH of the inoculated medium at the outset of the initial inoculation is within the range of 6.0–7.5, and the medium is normally maintained at a temperature of from about 60 to 115 degrees Fahrenheit during the initial and further incubation steps. As noted, the culture medium can be any one of a number of heretofore known media, but broadly should be in the form of an aqueous composition having milk-derived nutrients dispersed therein. As noted hereinafter, a particularly preferred medium includes whey and a minor amount of lecithin therein, and this medium has been shown to give advantageous results when used in conjunction with the methods hereof.

At the conclusion of the preferred procedure, the titratable acidity of the medium should be from about 0.5–1.8, and preferably from about 1.0–1.5. At this point the medium is cooled in order to terminate the incubation, typically to a temperature of from about 35–60 degrees Fahrenheit.

While the method hereof can be used to good utility in connection with a wide variety of cheese-making microorganisms, it is particularly preferred in conjunction with cultures used for the manufacture of Italian cheese such as mozzarella. In such case, the medium is inoculated with a mixture of coccus and rod microorganisms, and the overall process is carried out so that the final coccus to rod radio is from about 2:1 to 5:1.

As noted above, a serious practical problem encountered in connection with so-called internal pH systems stems from the need to continuously stir or agitate the starter tank during the incubation. It has been found, however, that the system of the present invention need not include such continual agitation, and indeed it is preferred that the medium be held essentially quiescent during the initial and further incubation steps referred to above.

In contrast to the external and internal pH systems, a graph of pH versus time in connection with the preferred process of the present invention will, generally speaking, resemble a "V". The first, downwardly extending leg of the "V" depicts the initial drop in pH, whereas the second, upwardly extending leg of the "V" represents the preferred, relatively sharp rise in pH which occurs upon the addition of base.

During the incubation after the pH level has been elevated, the pH again begins to drop because of acid production. Although it is within the ambit of the invention to again add base to elevate the pH when it drops to, e.g., below 5.0, it has been found that such additional pH elevations do not give any material advantages. Accordingly, it is preferred to have but a single pH elevation during incubation.

DESCRIPTION OF THE PREFERRED EMBODIMENT

The following examples illustrate the methods of the invention, and compare the same to prior methods in order to demonstrate the superiority of the pH modification hereof. It is to be understood, however, that the examples are for illustration purposes only insofar as they describe pH modification methods in accordance with the invention; therefore, nothing in these illustrative examples should be taken as a limitation upon the overall scope of the invention.

EXAMPLE 1

In this series of tests the efficacy of the method of the invention were tested as compared with the traditional method of microorganism growth, using a total of four separate starter media.

The media selected for this series of tests included: (1) nonfat dry milk solids dispersed in water to a 12% solids level; (2) a commercially available phage-resistant initially dry medium sold under the designation "Thermostar" by Marshall Division of the Miles Laboratories, and reconstituted in water to an 11% solids level; a commercially available phage-resistant, initially dry medium sold under the designation "Actilac" by Galoway West & Company of Fondulac, Wis., and reconstituted to a 11% solids level; and preferred test medium containing lecithin used at a 7% solids level.

The most preferred lecithin-containing starter media is initially in the form of a dried composition which is then added to an aqueous system to give a reconstituted liquid starter medium. This composition includes the following components:

TABLE I

| Ingredient | Initial Quantity[1] | Parts by Wt. of Dried Composition (Dry Basis) |
|---|---|---|
| Stimulant | 700 lbs. | 4.120 |
| Nonfat dry milk solids | 900 lbs. | 5.290 |
| Sodium tetra phosptate | 800 lbs. | 4.700 |
| Disodium phosphate | 550 lbs. | 3.230 |
| Monosodium phosphate | 800 lbs. | 4.700 |
| Manganese chloride | 400 gr. | 0.005 |
| Ferrous ammonium sulfate | 400 gr. | 0.005 |
| Lecithin[2] | 5 gallons | 0.290 |
| Sweet liquid | 280,000 lbs. | 77.660 |

TABLE I-continued

| Ingredient | Initial Quantity[1] | Parts by Wt. of Dried Composition (Dry Basis) |
|---|---|---|
| whey[3] | | |

[1]Total weight or quantity, including free water, of starting ingredients
[2]Lecithin in liquid form, 50% by wt. solids; or could be in the form of a dried powder
[3]May alternatively be derived by mixing 13,198 lbs of dried whey with 266,802 lbs. of water The preferred dried powder media composition is made as follows. In the first step, 700 pounds of the stimulant (a dried mixture of corn steep solids and sweet whey solids described in detail below), along with 900 pounds of the nonfat dry milk solids are mixed with the 280,000 pounds of sweet whey (either raw or pasteurized, normally pasteurized). After sufficient mixing to disperse the stimulant and milk solids, the mixture is neutralized by the addition of sodium hydroxide (50%) to a pH of 7. The pH-adjusted mixture is then thermally evaporated under vacuum conditions to a 41 percent solids level, whereupon the mixture is cooled to 50 degrees Fahrenheit and transferred to a final mixing tank.

A phosphate/minerals/lecithin premix is prepared separately from the mixture of stimulant, dried milk and whey. This premix is made by adding 375 gallons of water at 96 degrees Fahrenheit to a 1,000 gallon mixing tank. Next, 800 pounds of sodium tetra phosphate is added, followed by 800 pounds of monosodium phosphate and 550 pounds of disodium phosphate, all with constant agitation. The next step involves dissolving the 400 grams of ferrous ammonium sulfate and 400 grams of manganese chloride in a small amount of water, whereupon these minerals are added to the agitated mixture of water and phosphates. The 5 gallons of lecithin is then added to the premix tank, again with sufficient agitation to ensure homogeneity. This premix is then added to the mixture of whey, stimulant and dried milk solids, whereupon the overall mixture is agitated overnight and spray dried to about 4% moisture to yield a flowable, dried, powder-like material.

The stimulant referred to above is made by taking 280,000 pounds of separated raw whey from the cheesemaking vat (such amount of whey being a separate quantity from that used in the starter media per se listed in Table I), and adjusting the pH thereof to a level of about 8.0 with sodium hydroxide. The pH-adjusted whey is then evaporated to a 34 percent solids level, and cooled to 50 degrees Fahrenheit. The evaporated whey is then pumped into a tank containing 42,880 pounds of commercialy purchased corn steep liquor having a pH of 4.15. Such liquor is obtained from The Staley Corporation of Decatur, Ill., and has a 50 percent solids level. This creates a mixture containing about 60 percent by weight corn steep solids and 40 percent by weight whey solids. The 60 percent-40% mixture is then agitated overnight, filtered and spray dried to about 4 percent moisture. The resultant dried product is stored in 50 pound bags for subsequent use in the starter media.

All eight of the media samples (two per media) were heated to 190 degrees Fahrenheit and maintained at that temperature for 1 hour, followed by cooling to 102 degrees Fahrenheit. The media were then inoculated (1%) with a standard coccus and rod culture (*Streptococcus thermophilus* and *Lactobacillus bulgaris*) and incubated at 102 degrees Fahrenheit until the pH came down to about 4.8 (typically 5-7 hours). At that time, one sample of each media was quickly neutralized with food grade sterile 50 percent sodium hydroxide to rasie the pH thereof to 6.3-6.5. The respective incubations were then allowed to continue until all titratable acidities were greater than 1.0. In the case of the "Thermostar" media, the final titratable acidity level was 1.4, in accordance with the manufacturer's recommendations. After the appropriate titratable acidity levels had been reached, the incubations were terminated by cooling to 40 degrees Fahrenheit.

The cultures grown in the respective media were tested for pH, titratable acidity, total bacterial count, coccus/rod ratio, and activity, using conventional testing techniques. The results of these tests are set forth below in Table II wherein those media subjected to the described pH modification in accordance with the invention are referred to as "neutralized", and those allowed to incubate without pH modification are referred to as "control."

TABLE II

| Media | Final pH | Final Titratable Acidity | Coccus and Rod Ratio | Total Bacterial Count | Activity |
|---|---|---|---|---|---|
| Non-fat Dry Milk (Control) | 4.20 | 1.02 | 4:1 | $140 \times 10^7$ | 0.70 |
| Non-fat Dry Milk (Neutralized) | 4.25 | 1.09 | 3:1 | $220 \times 10^7$ | 0.84 |
| Thermostar (Control) | 4.25 | 1.40 | 1:1 | $100 \times 10^7$ | 0.60 |
| Thermostar (Neutralized) | 4.23 | 1.50 | 1:1 | $150 \times 10^7$ | 0.69 |
| Actilac (Control) | 4.15 | 1.08 | 1:1 | $160 \times 10^7$ | 0.73 |
| Actilac (Neutralized) | 4.12 | 1.04 | 1:1 | $250 \times 10^7$ | 0.82 |
| Lecithin Medium (Control) | 4.35 | 1.02 | 4:1 | $130 \times 10^7$ | 0.72 |
| Lecithin Medium (Neutralized) | 4.32 | 1.05 | 3:1 | $190 \times 10^7$ | 0.83 |

The foregoing results demonstrate that in all instances the method of the invention gave superior results. Baceterial counts were uniformly higher, as were activity readings. Coccus/rod ratios were not significantly altered as compared with the controls.

EXAMPLE II

In this example the effects of continuous neutralization and agitation on coccus/rod cultures were measured and compared with the effects of the methods of the invention.

Nonfat dry milk solids were reconstituted in water to 12% solids level and four 100 ml. samples thereof were prepared in respective dilution bottles. All media samples were then heated to 190 degrees Fahrenheit and maintained at that temperature for 1 hour followed by cooling to 102 degrees Fahrenheit. At this point the samples were inoculated at 102 degrees Fahrenheit with the coccus/rod microorganisms described above at a 1 percent level of inoculation.

The control media was simply allowed to inoculate without any pH modification until the titratable acidity level was greater than 1.0. At this point the medium was cooled to 50 degrees Fahrenheit.

The external pH control test involved continual mointoring of the pH of the medium sample and, when the pH fell to 6.0, it was adjusted upwardly to 6.3 using 50% sodium hydroxide. This procedure was continued for a period of time equal to the incubation time of the control, whereupon the medium was cooled to 50 degrees Fahrenheit.

The agitation test involved continual shaking of the incubated sample, but without any time release pH modification tablets or the like. Such continuous agitation is characteristic of the internal pH control systems described previously.

Finally, the last medium sample was incubated using the pH modification technique of the invention. This involved initial incubation and monitoring of the pH of the system until the pH reached 4.8, whereupon 50 percent sterile sodium hydroxide was added to quickly elevate the pH to a level of 6.3–6.5. The system was then further incubated without additional pH modification until the titratable acidity was greater than 1.0, whereupon the medium was cooled to 50 degrees Fahrenheit.

The results of this test are set forth in Table III:

TABLE III

| Media/ Treatment | Final pH | Final Titratable Acidity | Coccus/Rod Ratio | Total Bacterial Count | Activity |
| --- | --- | --- | --- | --- | --- |
| NFDM/ Control | 4.20 | 1.20 | 4:1 | $140 \times 10^7$ | 0.70 |
| NFDM/ External pH | 5.45 | 0.50 | 15:1 | $75 \times 10^7$ | 0.55 |
| NFDM/ Agitation | 4.90 | 0.75 | 7:1 | $63 \times 10^7$ | 0.51 |
| NFDM/pH Modification of Invention | 4.25 | 1.09 | 3:1 | $220 \times 10^7$ | 0.84 |

The results of Table III clearly demonstrate the improved results obtained through use of the method of the invention. For example, the continuous external pH control and agitation tests gave low titratable acidities and coccus/rod ratios which were unacceptable; in addition, baceterial counts and activities were significantly reduced. On the other hand, the method of the invention gave much improved results as compared with the external pH control and agitation systems, and also as compared to the traditional incubation method free of pH modification.

The various tests referred to in the foregoing Examples were performed as follows:

pH: Hydrogen ion concentration was determined using Beckman pH meter

Titratable Acidity: 9 grams of medium sample was thoroughly mixed and titrated with 0.1N sodium hydroxide using phenophthalein as an indicator. A faint pink color indicated the end point.

Coccus and Rod Ratio: A one in ten dilution of culture in water was smeared on a clean glass slide, stained with methylene blue and examined under a compound microscope. The ratio was determined on the basis of clump and individual counts.

Total Bacterial Count: The cultured samples were serially diluted in sterile phosphate buffered water according to the procedures outlined in the Standard Methods for the examination of dairy products and plated using tryptic soy agar fortified with 0.5% yeast extract. The plates were incubated at 37 degrees Centigrade for 4 days. The counting and expression of the test results were done according to the Standard Procedures.

Activity Test: 2 grams of culture was inoculated into 100 ml. of sterile 10.0 g. reconstituted nonfat dry milk. The nonfat dry milk was pretested for the inhibitory compounds. The inoculated milk was incubated at 36 degrees Centigrade for 45 minutes. At the end of incubation, the temperature was gradually increased to 46 degrees Centigrade within a span of 30 minutes and it was thereafter maintained at that temperature for a period of 1 hour. The samples were then chilled to prevent any further acid development. Ten grams of the sample was carefully weighed into a 25 ml. beaker. Ten drops of indicator (Phenophthalein) was added and the entire contents were titrated against 0.1N sodium hydroxide until a faint pink color persisted for 15 seconds. The results were expressed as percent titratable acidity.

I claim:

1. A method of growing acid-producing cheese-making microorganisms, comprising the steps of:

providing a cheese-making microorganism starter medium in the form of a liquid and having a major proportion of whey therein, the whey present in said medium initially and throughout said method consisting essentially of sweet whey;

inoculating a mixture of coccus and rod microorganisms into said medium;

initially incubating said microorganisms in said medium until the pH of the latter drops to a level of from about 3.9 to 5.5, said initial incubation step being carried out without neutralization of the acid produced during the initial incubation; and thereafter quickly raising the pH of said medium at least 1 pH unit, and further incubating said microorganisms in the medium with the final coccus to rod ratio of the microorganisms being from about 2:1 to 5:1. .

2. The method of claim 1, said initial incubation step being carried out until said medium has a pH of from about 4.5 to 5.3.

3. The method of claim 1, said pH raising step comprising the step of adding base to said medium.

4. The method of claim 3, said base being a hydroxide salt.

5. The method of claim 1, said medium being held essentially quiescent during said initial and further incubation steps.

6. The method of claim 1, said raising of said pH being accomplished during a period of up to about 3 minutes.

* * * * *